Figure 1:
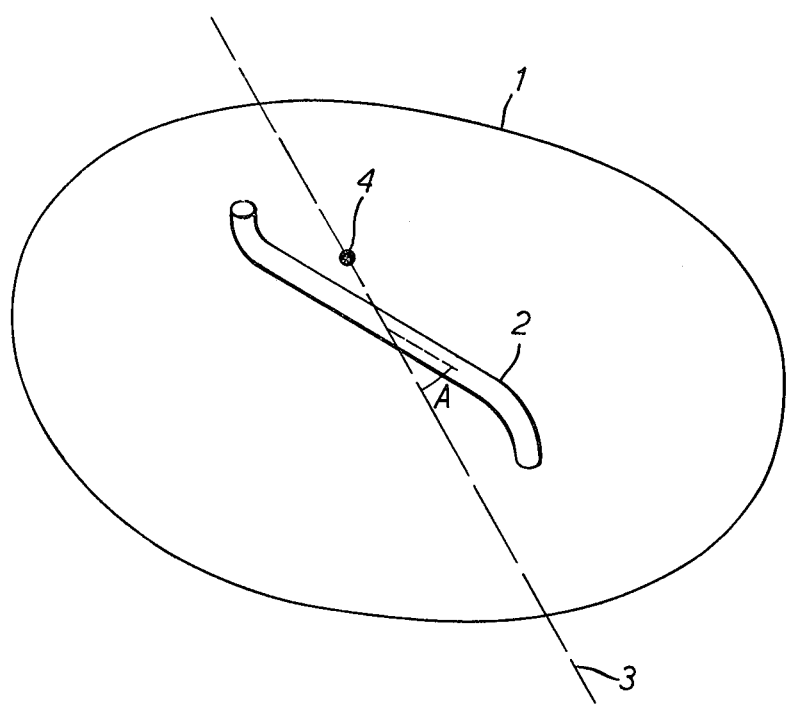

United States Patent [19]
Kossoff

[11] 3,939,707
[45] Feb. 24, 1976

[54] MEASUREMENT OF LIQUID FLOW

[75] Inventor: George Kossoff, Northbridge, Australia

[73] Assignee: The Commonwealth of Australia, Phillip, Australia

[22] Filed: May 15, 1974

[21] Appl. No.: 470,125

[30] Foreign Application Priority Data
May 15, 1973 Australia................................ 3316/73

[52] U.S. Cl........ 73/194 A; 128/2.05 F; 128/2.05 Z
[51] Int. Cl.²............................................ G01F 1/66
[58] Field of Search...... 73/194 A; 128/2 V, 2.05 F, 128/2.05 Z

[56] References Cited
UNITED STATES PATENTS

| 3,498,290 | 3/1970 | Shaw et al. | 73/194 A X |
| 3,554,030 | 1/1971 | Peronneau | 73/194 A |
| 3,777,740 | 12/1973 | Hokanson | 128/2 V |

OTHER PUBLICATIONS

D. W. Baker, "Pulsed Ultrasonic Doppler Blood-Flow Sensing", IEEE Transactions on Sonics and Ultrasonics, July 1970, pp. 170–184.

Primary Examiner—Charles A. Ruehl

[57] ABSTRACT

A method of pulse-echo ultrasonic examination of an object, particularly in medical diagnostic examination, to measure flow of liquid in a vessel within the object comprises determining the dimensions and orientation of the vessel and the shift in frequency of ultrasonic echoes due to flow of liquid in the vessel and correlating to obtain a quantitative measurement of the flow of liquid.

6 Claims, 1 Drawing Figure

U.S. Patent   Feb. 24, 1976   3,939,707

MEASUREMENT OF LIQUID FLOW

This invention relates to the technique of ultrasonic echoscopy of objects and in particular to an extension of known techniques of ultrasonic echoscopy to provide more useful information concerning the examined objects. It is particularly, but not solely, directed to the more effective acquisition of data in medical diagnosis utilizing this technique.

Ultrasonic echoscopy provides information about an examined object which may be displayed in the form of an ultrasonic echogram. Such an echogram consists of a display of acoustic impedance discontinuities or reflecting surfaces in the object. It is obtained by directing a short pulse of ultrasonic energy, typically in the 1–30 MHz frequency range generated for example by a transducer into the examined object where any acoustic impedance discontinuities in the object reflect and return some of the energy in the form of an echo. This echo is received, for example by a transducer, converted into an electric signal and displayed as an echogram on a cathode ray oscilloscope, a film, a chart or the like.

The echogram may constitute either a one dimensional or a two dimensional representation and in both cases the information is contained in the position and magnitude of the echo displayed. In a one dimensional display, the position along a base line is used to indicate the distance to the reflecting surface whilst the magnitude of the echo is displayed, for example, as a deflection of a base line or as an intensity change. In a two dimensional display, the position along a base line is used to indicate the distance to the reflecting surface as in a one dimensional display, and the direction of the base line is used to represent the direction of propagation of the acoustic energy. The two dimensional display is obtained by changing this direction of propagation of the acoustic energy and by instituting a similar but not necessarily identical movement of the base line of the display. The magnitude of the echo is displayed as for a one dimensional display; for example, as a deflection of the base line or as an intensity change.

The technique of ultrasonic echoscopy is used in medical diagnosis to obtain information about the anatomy of patients. The application of the technique is now widely investigated and is described, for example, by D. E. Robinson in Proceeding of the Institution of Radio and Electronics Engineers, Australia, Vol. 31, No. 11, pages 385 – 392, November, 1970; "The Application of Ultrasound in Medical Diagnosis." As pointed out in this article, ultrasonic echoscopy may be used to produce displays resembling anatomical cross-sections which have proved clinically useful when the desired information concerns physical dimensions, shapes of organs or structures or the like. Ultrasonic echography has proved of particular value as a diagnostic aid in the abdomen and pregnant uterus, eye, breast, brain, lung, kidney, liver and heart these being areas of soft tissue with little bone and air. In general, the technique is considered to complement other techniques to provide a more complete picture of the patient's condition, however particularly in pregnancies, ultrasonic echoscopy may be useful in place of X-rays where the latter may not give sufficient information or may be dangerous. In medical use, a pulse of ultrasonic energy is transmitted into a patient in a known direction and echoes are received from reflecting surfaces within the body. The time delay between a transmitted pulse and the received echo depends on the distance from the transmitter to the reflecting surface and the distance information so obtained may be displayed in a suitable way for interpretation and clinical use as a one dimensional range reading or as a two dimensional cross section as previously described.

If a pulse of ultrasound is propagated into a medium, echoes will be received at various time delays and these time delays will be proportional to the distances from the transducer producing the pulse to the interfaces provided the velocity of propagation is constant. In soft tissues found in the human body the velocity of sound is reasonably constant and pulsed ultrasound provides a convenient method of measuring the depth of a particular structure from the transducer face without inconvenience to the patient. This information can be used in a number of ways.

In the simplest form of display, "A mode," the echoes are presented as deflections of the trace of an oscilloscope in which distance is represented along the time axis. This mode is useful clinically when the source of the various echoes displayed can be positively identified. It is possible to measure the distance between two echoes or between the energizing pulse and an echo with accuracy but it may not be possible to identify the source of the echoes. It has been used to measure the size of the baby's head inside the uterus, the depth of the eye and the bladder and to locate the midline in the brain. Similar information may be displayed by use of the "B mode" where a cross sectional view is obtained by moving the transducer around the examined object and making the trace on the display follow a similar movement. A B mode display may be obtained either with simple or compound scanning. In the former the movement of the transducer is selected so that there is no superpositioning of lines of sight from different directions. Linear and sector scanning are typical examples of simple scanning. With compound scanning the movement of the transducer is selected so that there is superposition from different lines of sight, a combination of linear and sector scanning being a typical example of a compound scan.

If the interface of interest is moving, its position may be plotted with time ("M mode") by using the B mode presentation and allowing the time base to be swept at right angles to its direction so as to display the movements of the interface echo backwards and forwards along the time base. This is used to demonstrate the pulsatile movements of various parts of the heart and brain. If the B mode is used but the trace on the screen is made to represent the line of sight of the transducer and then the transducer is scanned around the patient and the time base line on the screen made to follow, a two-dimensional plot of impedance discontinuities is obtained. Two dimensional visualization has been used in the pregnant uterus, abdomen, eye and breast.

Coupling from the transducer to the patient may be achieved by skin contact or by use of a water delay bath. If a water delay bath is used the distance between the transducer and the skin surface must be greater than the largest depth of penetration to be used, to avoid ambiguity due to multiple reflection. In general the skin contact scan results in greater comfort for the patient and echograms of less clarity while the water delay scan gives less patient comfort and better quality echograms.

In order to compensate for the reduction in the energy of the ultrasonic pulse due to attenuation within the object under examination, for example tissue, the gain of the receiver is generally increased as the echo of the pulse is received from deeper reflecting surfaces within the object. This type of increase in gain is generally referred to as "time gain compensation" or "TGC". In some receivers, TGC amplification is also followed by a non-linear compression amplification to further compress the size of the echoes so that they may be more readily displayed on the display unit.

It is an object of the present invention to provide a method whereby the technique of ultrasonic echoscopy may be utilized for the measurement of the flow of liquids in vessels such as remote, intact tubes in an examined object.

According to the present invention, there is provided a method of ultrasonic examination of a vessel within an examined object to obtain a quantitative measurement of flow of liquid in the vessel, comprising the steps of a. transmitting pulses of ultrasonic energy into the object and receiving echoes of said pulses reflected by acoustic impedance discontinuities within the object, the pulses being transmitted and echoes received along a plurality of beams in a single plane, a portion of the vessel within the object lying in said plane, b. displaying said received echoes as a visualization of said portion of the vessel in said plane and determining the dimensions and orientation of said portion in said plane from the display, c. transmitting pulses of ultrasonic energy into said portion of the vessel along a beam in said plane at a measured angle to said portion and determining the shift in frequency of echoes of said pulses caused by flow of liquid in said portion, and d. correlating said shift in frequency with the dimensions of said portion of the vessel and said measured angle to obtain a measurement of the velocity of flow of the liquid in the vessel. As broadly described, a cross-sectional visualization of a portion of the vessel to be examined lying in the plane of the visualization is displayed, for example by conventional grey scale B mode visualization. In practice, it may be necessary to adjust the plane of scan so that a suitable plane is selected where the axis of the portion of the vessel of interest lies within the plane and the walls of the vessel are clearly displayed in the echogram. At this stage the diameter and other dimensions of the portion of the vessel and the angle of the axis with respect to a fixed direction in the scan plane can be measured.

A line of sight may then be selected within the established scan plane at a suitable known angle to this fixed direction and hence at a known angle to the axis of the portion of the vessel. The shift in frequency of echoes of pulses of ultrasonic energy directed along this line of sight caused by flow of liquid in the vessel is then determined using the known Doppler methods as disclosed, for instance, by D. W. Baker in "Pulsed Ultrasonic Doppler Blood Flow Sensing" (IEEE Transactions on Sonics and Ultrasonics Vol. SU-17 No. 3, July 1970). Calculation of the velocity of flow of liquid from the measured frequency shift with the measured vessel diameter and known angle may then be effected in accordance with known techniques, such as those disclosed by Baker.

As described above, ultrasonic B mode echoscopes are currently used to provide cross-sectional display of acoustic impedance discontinuities in the examined object. In particular it is possible to outline vessels carrying liquids and to measure the dimensions and orientations of these vessels in relation to the scanning ultrasonic beam. In medical applications arteries and veins are examples of such vessels. Doppler systems are currently used to measure the frequency shift in echoes caused by flow in the vessels, the shift being proportional to the velocity of the flow and the orientation of the examining beam to the vessel.

In one embodiment, the present invention relates to the combined use of B mode and Doppler technique for quantitative measurement of flow in the vessel. In a typical application, a transducer is first used in the B mode to obtain a cross-sectional display to outline the vessels in the examined object. From this display a line of sight is chosen which intercepts the selected vessel and the instrument is switched over to the Doppler mode operation to measure the frequency shift along that line of sight. It is possible that the same transducer may be used for both modes of operation but the present invention also encompasses the use of more than one transducer suitably positioned to perform the measurements. The invention also encompasses the use of either continuous or pulsed Doppler operation where the latter may be used to reduce spurious signals from flow in other vessels lying along the selected line of sight, the range of the pulsed Doppler system being adjusted to pick up signals either from the whole or portions of the selected vessel. The present invention also encompasses simultaneous operation of the B mode and Doppler system. The flow in the selected vessel may then be obtained from both sets of data i.e., orientation and cross-sectional area of the vessel from the B mode cross-sectional system and the frequency data from the Doppler system.

The invention is illustrated in FIG. 1 which represents the B mode echogram from the examined object. Outline 1 is the outside border of the part examined, and tube 2 carries the flowing liquid whose flow is to be measured. The B mode echogram allows the measurement of the diameter of the vessel to be measured. It is anticipated that in some circumstances several echograms at different levels may be employed to determine the full three dimensional geometry of the vessel. If necessary the position and angle of the scan plane are adjusted to obtain a satisfactory representation of the vessel with the axis of the vessel lying within the scan plane. The Doppler measurement is made either simultaneously or following the B mode measurement along the selected line of sight 3, which subtends an angle A with respect to the tube. In a preferred embodiment, the line of sight associated with the Doppler measurement may be displayed simultaneously with the B mode visualization to facilitate measurement of the angle A between the line of sight and the axis of the vessel. If necessary a range marker 4 is used in pulsed Doppler operation to set the range of the pulse Doppler measurement over the tube 2. The average velocity V is then obtained from the frequency data taking into account whether continuous or pulsed Dopper operation is employed, the nature of the flow in the vessel e.g. laminar, turbulent, and the angle of inclination of the vessel to the selected line of sight. For example in laminar flow the average velocity of the flow V is given by $$V = \frac{C \Delta f}{2 f_o \cos A}$$

where C is the velocity of the sound in the medium, $\Delta f$ the average Doppler difference frequency and $f_o$ the ultrasonic carrier frequency. The volume flow rate F is then given by $$F = \frac{D^2 V}{4}$$

where D is the diameter of tube 2.

From the foregoing description it will be therefore appreciated that the present invention enables additional useful data to be acquired by ultrasonic examination of objects. While the invention has been described with reference to one particular embodiment, it will be generally understood by those skilled in the art that various modifications and variations may be made without departing from the true spirit and scope of the invention.

What I claim is:

1. A method of ultrasonic examination of a vessel within an examined object to obtain a quantitative measurement of flow of liquid in the vessel, comprising the steps of:
   a. transmitting pulses of ultrasonic energy into the object and receiving echoes of said pulses reflected by acoustic impedance discontinuities within the object, the pulses being transmitted and echoes received along a plurality of beams in a single plane, the axis of a portion of the vessel within the object lying in said plane;
   b. displaying said received echoes as a visualization of said portion of the vessel in said plane;
   c. transmitting pulses of ultrasonic energy into said portion of the vessel along a beam in said plane at an angle to the axis of said portion and determining the shift in frequency of echoes of said pulses caused by flow of liquid in said portion;
   d. determining from the display the diameter of said portion of the vessel in said plane and the angle between the axis of said portion and the beam along which the shift of frequency is determined; and
   e. correlating said shift in frequency with the diameter of said portion of the vessel and said angle to obtain a measurement of the velocity of flow of liquid in the vessel.

2. A method according to claim 1, wherein a single transducer is used to obtain the echoes in both step (a) and step (c).

3. A method according to claim 1 wherein independent transducers are used to obtain the echoes in step (a) and step (c).

4. A method according to claim 1, wherein steps (a) and (b) are performed before step (c).

5. A method according to claim 1, wherein the orientation of the longitudinal axis of said portion of the vessel in said plane is determined from said display, and the shift in frequency determined in step (c) is determined along a beam at a selected angle to the axis of said portion.

6. A method according to claim 1, wherein steps (a) and (c) are performed simultaneously.

* * * * *